Dec. 8, 1953 W. E. PINCHBECK Plant Pat. 1,232
ROSE PLANT
Filed Oct. 31, 1952
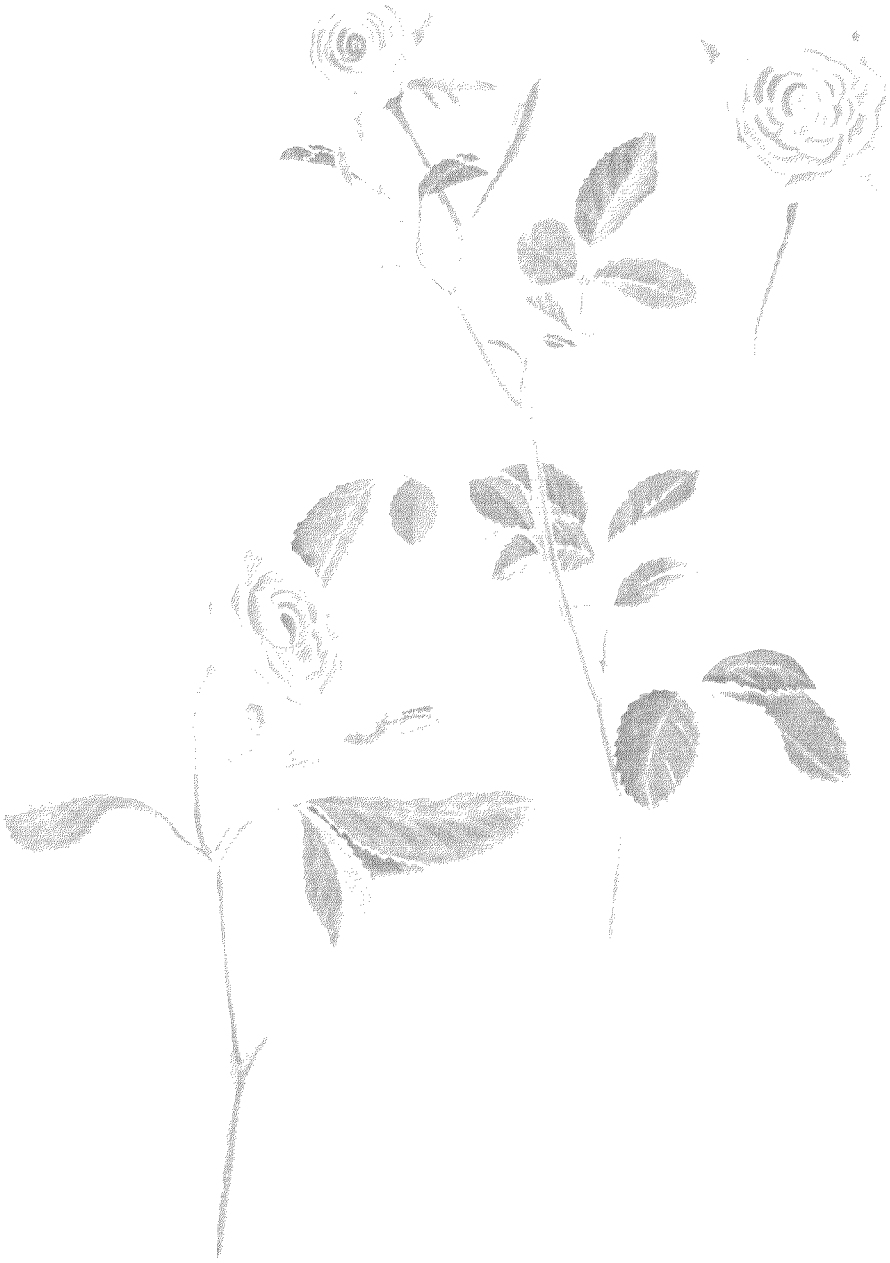
INVENTOR
William E. Pinchbeck
By Orville M. Kile
Plant Patent Agt Patented Dec. 8, 1953

Plant Pat. 1,232

UNITED STATES PATENT OFFICE 1,232

ROSE PLANT

William E. Pinchbeck, Guilford, Conn., assignor to William Pinchbeck, Inc., Guilford, Conn.

Application October 31, 1952, Serial No. 318,134

1 Claim. (Cl. 47—61)

My present discovery pertains to a new and distinct variety of rose plant of the polyantha type, which is a cultivated pink sport of the variety Garnette (unpatented) and originated in my nurseries at Guilford, Connecticut.

I have asexually reproduced the new variety at the same location by means of cuttings, and its distinguishing features appear to be permanent.

This new variety is similar to its parent in many respects but its flower is pink in color whereas that of its parent is bright red. Also the forms of the flowers of the two varieties differ, particularly in the early stages of opening, in that the form of the flower of my new variety is more globular in its early stages, then becoming flat-topped and later cupped, as compared with the parent flower which is high-centered with slightly reflexed petals in the early stages of opening and becomes imbricated in later stages. The foliage of my variety also differs in that the individual leaves are smaller and not so pointed as those of the parent variety.

Accompanying illustrations are water-color paintings of three specimens of the bloom of my new variety in various positions and stages of opening, together with portions of the stems and foliage—all in approximately true colors.

In the following detailed description, color plate numbers refer to Ridgway's Color Standards and Nomenclature.

*The plant*

Growth: Dwarf, bushy, growing to approximately 2 feet in height. Breaks freely.

Blooming habit: Continuous and prolific bloomer.

Borne: Singly, but occasionally in clusters.

Stems:

*Color.*—Approximately Spinach Green (Pl. V).

*Type.*—Zigzagged, with short internodes.

*Strength.*—Slender but strong.

*Thorns.*—Absent on upper stem but numerous on lower portion. Sharp; greenish-colored; downward-pointing; irregularly spaced.

Foliage:

*Leaves.*—Mostly 3 to 5 leaflets with terminal leaflet considerably larger than lateral leaflets—the last laterals next to stem being much smaller.

*Size.*—Terminal leaflets are usually 1½ to 2 inches long by 1 to 1¼ inches wide.

*Shape.*—Broadly oval, with rounded base and tip, with only slight point at apex. Edges sharply serrated.

*Texture.*—Leathery but not heavy.

*Color.*—Forest Green to Elm Green (Pl. XVII) on upper surface; under surface much lighter. New foliage red or tinged with red, approximately Pompeian Red (Pl. XIII).

*Rachis.*—Slender; grooved and reddish-tinged on upper side; occasional small thorn on under side.

*Stipules.*—Adnate; small; points slender and long.

*The bloom*

The bud:

*Size.*—Small; ¾ to 1 inch long.

*Shape.*—Pointed when very small and before calyx breaks, but stubby and depressed in center after color shows and bud begins to open.

*Sepals.*—Relatively simple but slightly branching; hood above very small bud.

*Peduncle.*—Short; slender but strong.

The flower:

*Size.*—Small, measuring about 2 inches in diameter when fully open.

*Form.*—In partly-open stage the form is somewhat globular with petals curving inward; later it appears flat-topped, with shell-like petals loosely arranged so that each row appears to be distinctly separated from the others, and the petals are neither reflexed nor imbricated as in some similar varieties. At a still later stage it opens in cupshape with stamens showing.

*Petalage.*—In the Fall months the petalage is approximately 55 petals.

*Longevity.*—Flower lasts well both on the bush and as a cut flower.

*Fragrance.*—Delicate.

*Color.*—There is considerable variation in shade of pink among the individual specimens, but on an average the color is Deep Rose Pink (Pl. XII) throughout when first opening; a little later, between Deep Rose Pink (Pl. XII) and Spinel Pink (Pl. XXVI); and finally becoming Rose Pink to Thulite Pink (Pl. XXVI) on the inner surface of the petals. The outer surface is lighter on most of the specimens and both surfaces show a large white aiglet.

Petals:

*Size.*—Outer petals average ¾ to 1 inch long and ¾ inch wide.

*Shape.*—Outer petals almost round, with inner petals narrower and smaller.

*Arrangement.* — Overlapping in partlyopened flower, but loose and separated or cupped in open flower.

*Texture.*—Soft and silky; substantial without being heavy.

Reproductive organs:

*Pistils.*—Many, bunched in center of flower. *Styles* greenish-white and of uneven lengths. *Stigmas* greenish-yellow.

*Stamens.*—Many; surrounding pistils. *Filaments* irregular in length. *Anthers* light yellow, approximately Empire Yellow (Pl. IV).

*Comparison*

The variety in the pink-flowered polyantha class known to me which is most like my new variety is the variety Carol Amling (Plant Patent No. 1126), but they differ principally as follows:

1. The bud of my variety is not so long.

2. Flowers of my variety are not so large and do not have so great a number of petals.

3. Flowers of my variety are somewhat different in form in that the petals of my variety stand apart from each other in the open flower, whereas those of Carol Amling are imbricated and usually somewhat reflexed.

4. Color of the flowers of the two varieties differs slightly, the color of my new variety being a little darker when grown under the same or similar conditions.

5. The fragrance of the flower of my variety is more delicate.

6. The individual leaves of the foliage of my new variety are not so large and are proportionately broader than the leaves of Carol Amling.

Having thus disclosed my discovery, I claim:

The new and distinct variety of polyantha rose plant, substantially as herein shown and described, characterized particularly by its prolific and continuous blooming habit; its freedom of breaking to produce abundant bushy growth; its small-leafed foliage; its short bud; and its pink flower of loose, flat-topped form.

WILLIAM E. PINCHBECK.

No references cited.